United States Patent
Nakayama et al.

(10) Patent No.: US 10,007,012 B2
(45) Date of Patent: Jun. 26, 2018

(54) X-RAY COMPUTED TOMOGRAPHY APPARATUS AND X-RAY DETECTOR

(71) Applicant: Toshiba Medical Systems Corporation, Otawara-shi (JP)

(72) Inventors: Michito Nakayama, Utsunomiya (JP); Atsushi Hashimoto, Otawara (JP); Tomoe Sagoh, Nasushiobara (JP); Takaya Umehara, Kawasaki (JP); Shuya Nambu, Nasushiobara (JP); Koichi Miyama, Nasushiobara (JP); Takashi Kanemaru, Yaita (JP); Keiji Matsuda, Nasushiobara (JP); Machiko Iso, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 192 days.

(21) Appl. No.: 14/994,809

(22) Filed: Jan. 13, 2016

(65) Prior Publication Data

US 2016/0219686 A1    Jul. 28, 2016

(30) Foreign Application Priority Data

Jan. 22, 2015  (JP) ................................. 2015-010480
Jan. 4, 2016   (JP) ................................. 2016-000244

(51) Int. Cl.
*G06K 9/00* (2006.01)
*G01T 1/24* (2006.01)
(Continued)

(52) U.S. Cl.
CPC ............ *G01T 1/2985* (2013.01); *A61B 6/032* (2013.01); *A61B 6/42* (2013.01); *G01N 23/046* (2013.01);
(Continued)

(58) Field of Classification Search
CPC ......... A61B 6/027; A61B 6/03; A61B 6/4233; A61B 6/425; A61B 6/4266; A61B 6/52;
(Continued)

(56) References Cited

U.S. PATENT DOCUMENTS 6,701,000 B1 *  3/2004  Hsieh ................... G01N 23/046
                                                  378/12

FOREIGN PATENT DOCUMENTS

JP    2002-94380     3/2002
JP    2005-347932   12/2005

* cited by examiner

*Primary Examiner* — Don Wong
(74) *Attorney, Agent, or Firm* — Oblon, McClelland, Maier & Neustadt, L.L.P.

(57) ABSTRACT

According to one embodiment, the X-ray computed tomography apparatus includes an X-ray tube, a rotating frame, a plurality of detector elements, a plurality of DAS elements, switching circuitry, and switching control circuitry. The X-ray tube generates X-rays. The X-ray tube is attached to the rotating frame. The plurality of detector elements detect X-rays. The plurality of DAS elements perform signal processing on output signals from the plurality of detector elements. The switching circuitry is provided between the plurality of detector elements and the plurality of DAS elements. The switching control circuitry controls the switching circuitry to switch the connections between the plurality of detector elements and the plurality of DAS elements for every rotation of the rotating frame at a predetermined angle.

15 Claims, 6 Drawing Sheets

(51) Int. Cl.
　　　*G01T 1/29*　　　　(2006.01)
　　　*A61B 6/03*　　　　(2006.01)
　　　*G01T 1/17*　　　　(2006.01)
　　　*G01N 23/046*　　(2018.01)
　　　*A61B 6/00*　　　　(2006.01)

(52) U.S. Cl.
　　　CPC .......... *G01T 1/17* (2013.01); *G01N 2223/304* (2013.01)

(58) Field of Classification Search
　　　CPC .... A61B 6/58; A61B 6/466; G01N 2223/427; G01N 2223/426; G06T 11/005; G06T 11/008; G06T 5/00
　　　USPC ...................... 382/130, 132, 131; 378/4, 901
　　　See application file for complete search history.

| View | First PD element (PD1) | Second PD element (PD2) |
|---|---|---|
| 1 | PD1-DAS1 (SW11···ON, SW12···OFF) | PD2-DAS2 (SW21···OFF, SW22···ON) |
| 2 | PD1-DAS2 (SW11···OFF, SW12···ON) | PD2-DAS1 (SW21···ON, SW22···OFF) |
| 3 | PD1-DAS1 (SW11···ON, SW12···OFF) | PD2-DAS2 (SW21···OFF, SW22···ON) |
| ⋮ | ⋮ | ⋮ |

F I G. 5

F I G. 6

| View | First PD element (PD1) | Second PD element (PD2) |
|---|---|---|
| 1 | PD1-DAS1 (SW11···ON, SW12···OFF, SW13···OFF) | PD2-DAS2 (SW21···OFF, SW22···ON, SW23···OFF) |
| 2 | PD1-DAS2 (SW11···OFF, SW12···ON, SW13···OFF) | PD2-DAS1 (SW21···ON, SW22···OFF, SW23···OFF) |
| 3 | PD1-DAS1 (SW11···ON, SW12···OFF, SW13···OFF) | PD2-DAS2 (SW21···OFF, SW22···ON, SW23···OFF) |
| ⋮ | ⋮ | ⋮ |

F I G. 7

| View | First PD element (PD1) | Second PD element (PD2) |
|---|---|---|
| 1 | PD1-DAS1 (SW11···ON, SW12···OFF, SW13···OFF) | PD2-DAS3 (SW21···OFF, SW22···OFF, SW23···ON) |
| 2 | PD1-DAS3 (SW11···OFF, SW12···OFF, SW13···ON) | PD2-DAS1 (SW21···ON, SW22···OFF, SW23···OFF) |
| 3 | PD1-DAS1 (SW11···ON, SW12···OFF, SW13···OFF) | PD2-DAS3 (SW21···OFF, SW22···OFF, SW23···ON) |
| ⋮ | ⋮ | ⋮ |

F I G. 8

| View | First PD element (PD1) | Second PD element (PD2) |
|---|---|---|
| 1 | PD1-DAS1 (SW11···ON, SW12···OFF, SW13···OFF) | PD2-DAS2 (SW21···OFF, SW22···ON, SW23···OFF) |
| 2 | PD1-DAS3 (SW11···OFF, SW12···OFF, SW13···ON) | PD2-DAS1 (SW21···ON, SW22···OFF, SW23···OFF) |
| 3 | PD1-DAS2 (SW11···OFF, SW12···ON, SW13···OFF) | PD2-DAS3 (SW21···OFF, SW22···OFF, SW23···ON) |
| 4 | PD1-DAS1 (SW11···ON, SW12···OFF, SW13···OFF) | PD2-DAS2 (SW21···OFF, SW22···ON, SW23···OFF) |
| ⋮ | ⋮ | ⋮ |

F I G. 9

F I G. 10

_X-RAY COMPUTED TOMOGRAPHY APPARATUS AND X-RAY DETECTOR_

CROSS-REFERENCE TO RELATED APPLICATIONS

This application is based upon and claims the benefit of priority from the prior Japanese Patent Application No. 2015-010480, filed Jan. 22, 2015, and No. 2016-000244, filed Jan. 4, 2016, the entire contents of all of which are incorporated herein by reference.

FIELD

Embodiments described herein relate generally to an X-ray computed tomography apparatus and an X-ray detector.

BACKGROUND

An X-ray computed tomography apparatus has an X-ray detector which detects X-rays and outputs digital data (raw data) in accordance with an intensity of the detected X-rays. The X-ray detector includes a data acquisition system (DAS) having a detector element array of a plurality of detector elements for detecting X-rays and a plurality of DAS elements for converting output signals from the plurality of detector elements into raw data.

Due to recent technological innovations, imaging with reduced X-ray dosages is being conducted more frequently. Usually, the dynamic range of the DAS is between $2^{18}$ and $2^{20}$; however, there are more and more instances of imaging with X-ray conditions of less than $2^{10}$. In such a low dosage region, the performance advantages and disadvantages of the DAS such as circuitry noise, linearity of the X-ray detector, aging drift, temperature drift, and crosstalk, etc., cause image artifacts.

The plurality of detector elements and the plurality of DAS elements are respectively connected on a one-to-one basis. Accordingly, if there is a variation in performance among the plurality of detector elements and DAS elements, the variation causes image artifacts. Furthermore, the number of detector elements and DAS elements are increasing year by year, and the increase of the number of detector elements leads to a higher rate of X-ray detector failure. Since the failure rate of DAS elements is higher than that of detector elements, image artifacts due to the variation in performance among the DAS elements tend to increase, as the number of elements increases.

DETAILED DESCRIPTION

In general, according to one embodiment, the X-ray computed tomography apparatus includes an X-ray tube, a rotating frame, a plurality of detector elements, a plurality of DAS elements, switching circuitry, and switching control circuitry. The X-ray tube generates X-rays. The X-ray tube is attached to the rotating frame. The plurality of detector elements detect X-rays. The plurality of DAS elements perform signal processing on output signals from the plurality of detector elements. The switching circuitry is provided between the plurality of detector elements and the plurality of DAS elements. The switching control circuitry controls the switching circuitry to switch the connections between the plurality of detector elements and the plurality of DAS elements for every rotation of the rotating frame at a predetermined angle.

In the following, the X-ray computed tomography apparatus and the X-ray detector according to the present embodiment will be explained with reference to the drawings.

Figure 1:
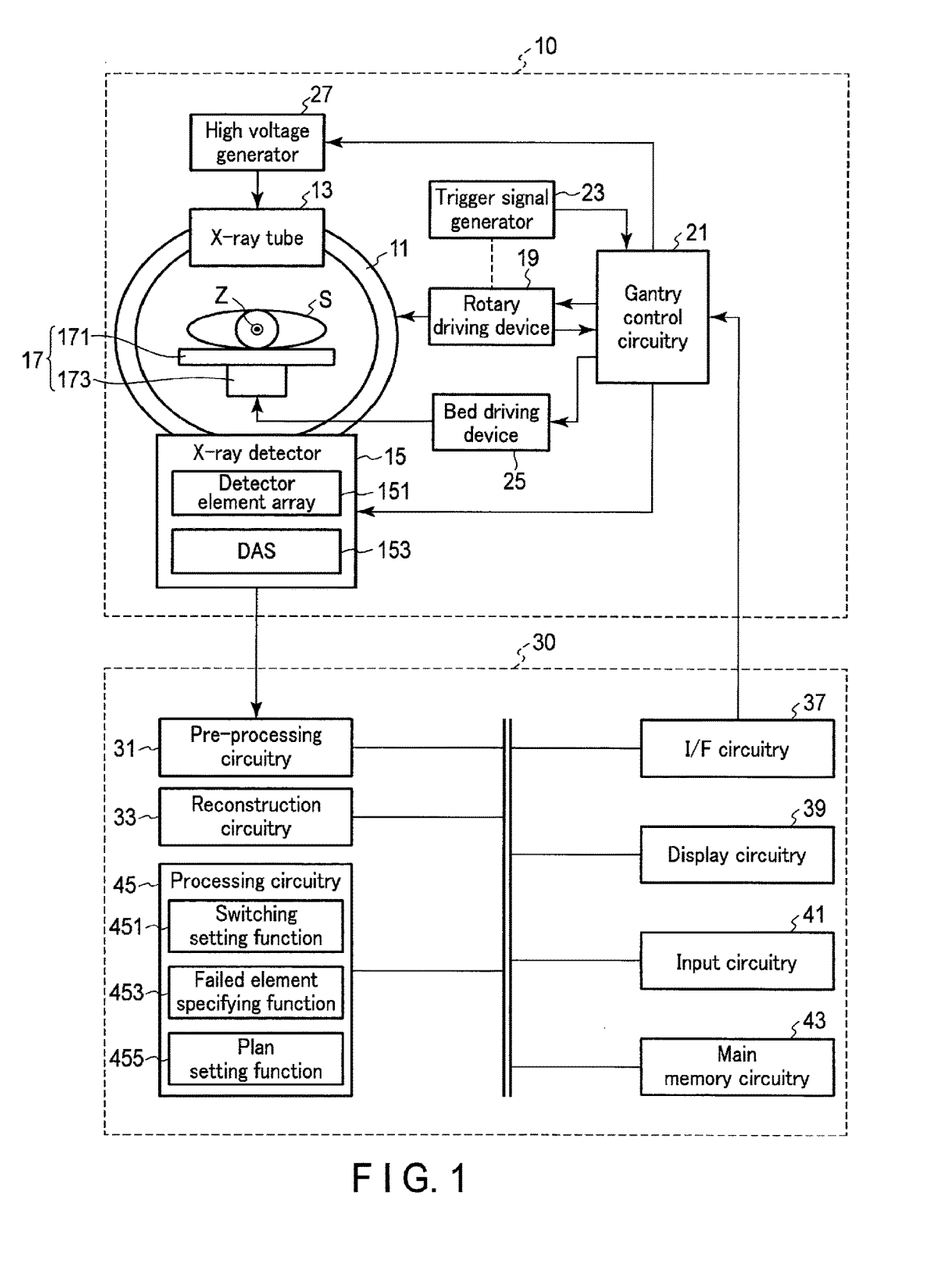
FIG. 1 shows a configuration of an X-ray computed tomography apparatus according to the present embodiment.

FIG. 1 shows a configuration of the X-ray computed tomography apparatus according to the present embodiment. As shown in FIG. 1, the X-ray computed tomography apparatus 1 has a gantry 10 and a console 30.

The gantry 10 rotatably supports the rotating frame 11 having a cylindrical shape with respect to a rotation axis Z. The X-ray tube 13 and X-ray detector 15 are attached to the rotating frame 11 in a manner so that the X-ray tube 13 and the X-ray detector 15 are opposed to each other with respect to the rotation axis Z. An Field of View (FOV) is set at the bore of the rotating frame 11. A bed 17 is inserted in the bore of the rotating frame 11. A subject S lies on the bed 17. The rotating frame 11 rotates about the rotation axis Z at a certain angular speed upon receiving a power from a rotary driving device 19. The rotary driving device 19 is realized by a motor which generates power to rotate the rotating frame 11 in accordance with control signals from gantry control circuitry 21. A trigger signal generator 23 is attached to the rotary driving device 19. The trigger signal generator 23 repeatedly generates electric pulse signals (hereinafter, referred to as "view trigger signals") every time the rotating frame 11 rotates at a predefined angle. The view trigger signals are supplied to the gantry control circuitry 21. A unit of time between view trigger signals is called a "view". A view is a minimal unit in which an output of the detector element array 151 is processed at the DAS 153.

The bed 17 has a top 171 upon which the subject S lies, and a top supporting frame 173 which moves freely and supports the top 171. For example, the top supporting frame 173 has a supporting mechanism which movably supports the top 171 in the rotation axis Z direction, the vertical direction, and the horizontal direction. The top supporting frame 173 moves the top 171 in a selectable direction upon receiving power from the bed driving device 25. The bed driving device 25 is a motor which moves the top 171 in a selectable direction in accordance with control from the gantry control circuitry 21. The bed driving device 25 is housed in the top supporting frame 173, for example.

The X-ray tube 13 generates X-rays upon application of a high voltage and a supply of a filament current from a high voltage generator 27. The high voltage generator 27 applies a high voltage to the X-ray tube 13 in accordance with a control signal from the gantry control circuitry 21, and supplies a filament current to the X-ray tube 13.

The X-ray detector 15 detects X-rays generated from the X-ray tube 13, and generates a digital signal (hereinafter, referred to as raw data) having a digital value corresponding to the detected X-rays. The X-ray detector 15 includes the detector element array 151 and the DAS 153. The detector elements array 151 includes a plurality of detector elements arranged in a two-dimensional manner. Each detector element detects X-rays generated from the X-ray tube 13, and generates an electric signal having a peak value corresponding to the intensity of the detected X-rays. The DAS 153 is integrated circuitry in which circuitry elements for performing signal processing on electrical signals from the plurality of detector elements are installed. The DAS 153 reads electric signals from the plurality of detector elements and converts the read electric signals into raw data. The raw data is transmitted to the console 30.

Figure 2:
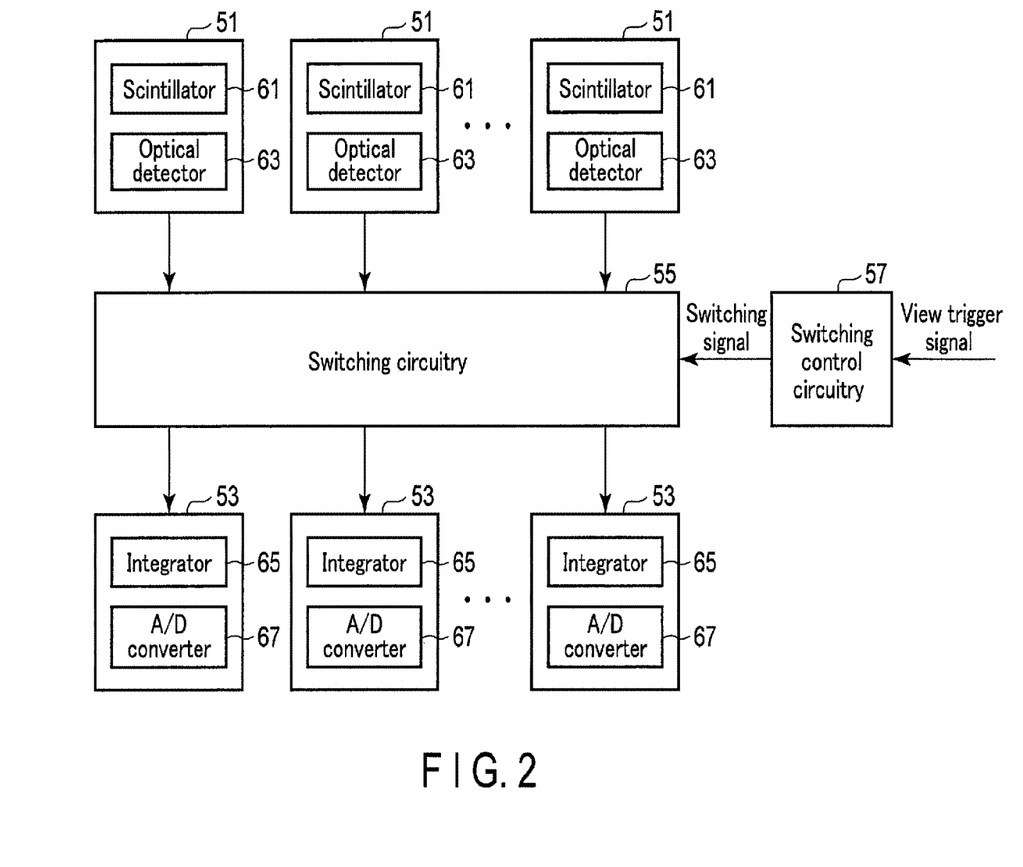
FIG. 2 shows a configuration of an X-ray detector shown in FIG. 1.

FIG. 2 shows a configuration of the X-ray detector 15. As shown in FIG. 2, the X-ray detector 15 includes a plurality of detector elements 51, a plurality of DAS elements 53, switching circuitry 55, and switching control circuitry 57.

Each detector element detects X-rays generated from the X-ray tube 13, and generates an electric signal having a peak value corresponding to the intensity of the detected X-rays. Any existing element that detects X-rays, such as a direct conversion-type element and an indirect conversion-type element, can be utilized as the detector element 51. Hereinafter, assume the detector element 51 is an indirect-conversion type element. The indirect-conversion type detector element 51 has a scintillator 61 and an optical converter 63. The scintillator 61 is a light-emitting material which absorbs X-rays and emits fluorescence. The optical converter 63 converts fluorescence from the scintillator 61 into current signals. As the optical converter 63, a photodiode or a photomultiplier tube is used.

The DAS element 53 is connected to the detector element 51 via a conductive wire, etc. The DAS element 53 is a circuitry element that performs signal processing on electric signals from the detector element 51. The DAS element 53 may be an energy-integral mode DAS element or a photon-counting type DAS element. In the following, for the sake of specific explanation, assume the DAS element 53 is an energy-integral type. As shown in FIG. 2, the DAS element 53 includes an integrator 65 and an A/D converter 67. The integrator 65 integrates (accumulates) the electric signals from the detector elements 51 for a certain period of time corresponding to one view, and outputs an integral signal having a peak value corresponding to a dosage of incident X-rays over one view. The integrator 65 is connected to the A/D converter 67 via the conductive wire, etc. The A/D converter 67 reads the integral signal from the integrator 65 and performs A/D conversion on the integral signals to output digital raw data.

The switching circuitry 55 is provided between the plurality of detector elements 51 and the plurality of DAS elements 53, and they are connected on a multiple-to-multiple basis. A connection relationship on a multiple-to-multiple basis is a relationship in which each detector element 51 is connectible to two or more DAS elements 53 via the switching circuitry 55. In such a connection relationship on a multiple-to-multiple basis, each DAS element 53 is connected to two or more detector elements 51 via the switching circuitry 55. One detector element 51 may be connected to at least two DAS elements 53. The DAS elements 53 connected to one detector element 51 may be all DAS elements 53 included in the DAS 153, or a part of the DAS elements 53. The switching circuitry 55 includes a plurality of switching elements. Each of the switching elements SW is provided between each detector element 51 and each respective DAS element 53, and upon a supply of a switching signal from the switching control circuitry 57, each switching element closes (ON) or opens (OFF) the connect ion between the detector element 51 and the DAS element 53. These switching elements may be provided in the DAS 153, or in the detector element array 151, or in any part in the gantry 10. The switching element closes upon a supply of an ON signal from the switching control circuitry 57, and opens upon a supply of an OFF signal. The switching of the switching elements is realized by a hardware description language (HDL), for example.

The switching control circuitry 57 controls the switching circuitry 55 to switch the connections between the plurality of detector elements 51 and the plurality of DAS elements 53 at every view, and disperses over multiple views the DAS elements 53 which are the destinations to which the respective detector elements 51 connect to. Specifically, the switching control circuitry 57 switches the DAS element 53 which is a connection destination for the detector element 51 in synchronization of a view trigger signal generated by the trigger signal generator 23. In each view, the plurality of detector elements and the plurality of DAS elements are connected on a one-to-one basis. In other words, each detector element 51 is connected to one DAS element 53, and in one view, each DAS element 53 is connected to one detector element 51. The switching control circuitry 57 supplies an ON signal to the switching elements to close, and an OFF signal to open.

Figure 3:
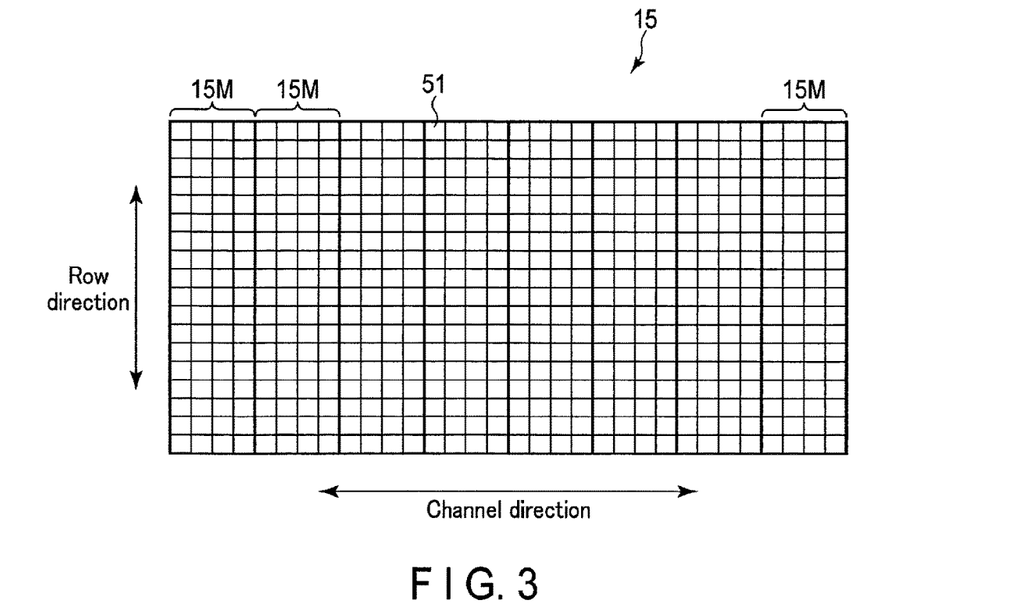
FIG. 3 is a plane view of the X-ray detector shown in FIG. 1.

FIG. 3 is a plain view of the X-ray detector 15. It should be noted that the row direction is defined as a direction parallel to the rotation axis Z, and the channel direction is defined as a circumferential direction of the rotating frame 11. As shown in FIG. 3, the X-ray detector 15 includes a plurality of detector modules 15M aligned along the channel direction. The plurality of detector modules 15M are provided in a separately detachable manner. Each detector module 15M includes the detector element array 151 and the DAS 153, and is a semiconductor substrate having a function of an X-ray detector 15. Each detector module 15M includes the detector elements 51 and the DAS elements 53 in accordance with the number in a design; for example, each of the detector modules 15M has 24 detector elements 51 and 24 DAS elements 53. As shown in FIG. 3, the plurality of detector modules 15M are aligned in a manner so that the plurality of detector elements 51 are aligned on the surface of the X-ray detector 15. When a DAS element 53 fails, instead of an entire X-ray detector 15, a detector module 15M including the failed DAS element 53 is replaced. It should be noted that the detector element arrays 151 and the DAS 153 may be respectively divided into multiple modules. In this case, the DAS module including the failed DAS element 53 will be replaced.

This concludes the explanation of the configuration of the X-ray detector 15.

As shown in FIG. 1, in accordance with the instructions from the processing circuitry 45 of the console 30, the gantry control circuitry 21 controls the controls at each device installed on the gantry 10. Specifically, the gantry control circuitry 21 controls the X-ray detector 15, the rotary driving device 19, a bed driving device 25, and the high voltage generator 27 in a synchronous manner. Specifically, the gantry control circuitry 21 controls the rotary driving device 19 in a manner so that the rotating frame 11 rotates at a predetermined angular speed. The gantry control circuitry 21 controls the DAS 153 and a high voltage generator 27 in synchronization with a supply of a view trigger signal from the trigger signal generator 23. The high voltage generator 27 generates an X-ray from the X-ray tube 13 in accordance with control by the gantry control circuitry 21. The DAS 153 acquires raw data via the X-ray detector 15 in accordance with control by the gantry control circuitry 21. In more detail, as described in the above, the switching control circuitry 57 of the DAS 153 controls the switching circuitry 55 to switch connections between the plurality of detector elements 51 and the plurality of DAS elements 53 at every view. The gantry control circuitry 21 controls the bed driving device 25 to move the top 171 in accordance with an input from a user via input circuitry 41, which will be described later. For example, by controlling the bed driving device 25 with the gantry control circuitry 21, the top 171 is positioned so as to include a scan target region of the subject S in FOV. The high voltage generator 27 may consecutively generate an X-ray during a data acquisition period.

The console 30 includes a preprocessing circuitry 31, reconstruction circuitry 33, I/F circuitry 37, display circuitry 39, input circuitry 41, main memory circuitry 43, and processing circuitry 45.

As hardware resources, the preprocessing circuitry 31 includes a computing device, such as CPU or MPU, and a memory device, such as ROM or RAM. The preprocessing circuitry 31 performs preprocessing including logarithmic transformation for the raw data transmitted from the gantry 10. The preprocessed raw data is called projection data. The preprocessing includes various correction processes, such as logarithmic transformation, X-ray intensity correction, and offset correction, etc.

As hardware resources, the reconstruction circuitry 33 includes a computing device, such as CPU or MPU, and a memory device, such as ROM or RAM. The reconstruction circuitry 33 generates a CT image expressing a spatial distribution of CT values related to the subject S based on the preprocessed raw data. As an image reconfiguration algorithm, any known image reconstruction algorithm, such as an analytical image reconfiguration method (e.g., a filtered back projection (FBP) method and a convolution back projection (CBP) method), and a statistical image reconstruction method (e.g., a maximum likelihood expectation maximization (ML-EM) method and an ordered subset expectation maximization (OS-EM) method) may be adopted. The reconstruction circuitry 33 may generate a sinogram based on the raw data. A sinogram indicates a distribution of data values in accordance with the intensity of the detected X-ray in a two-dimensional space defined by the view direction and the channel direction (or the row direction).

It should be noted that the preprocessing circuitry 31 and the reconstruction circuitry 33 maybe incorporated into a single hardware resource.

The I/F circuitry 37 is an interface for communications between the console 30 and the gantry 10. For example, the I/F circuitry 37 transmits a switching pattern set by a switching setting function 451 to the gantry 10. The I/F circuitry 37 also transmits a preset scanning condition to the gantry 10.

The display circuitry 39 displays a CT image and a screen for setting a scan plan, etc. on a display device. A CRT display, a liquid crystal display, an organic EL display, a plasma display, etc. can be suitably used as, for example, a display device.

The input circuitry 41 accepts various instructions and information inputs from a user via an input device. A keyboard, a mouse, and various switches may be used as an input device.

The main memory circuitry 43 is a memory device, such as a hard disk drive (HDD) for storing various information. For example, the main memory circuitry 43 stores the raw data before preprocessing, the preprocessed raw data, and CT image data. The main memory circuitry 43 stores a program for the switching setting and a scan program, etc. according to the present embodiment.

The preprocessing circuitry 45 includes a computing device, such as a CPU or MPU, and a memory device, such as ROM or RAM, as hardware resource. The process circuitry 45 functions as a center of the X-ray computed tomography apparatus 1. Specifically, the process circuitry 45 reads a control program stored in the main memory circuitry 43 and expands it in a memory, and controls the respective units of the X-ray computed tomography apparatus 1 in accordance with the expanded control program.

The processing circuitry 45 realizes the switching setting function 451, a failed element specifying function 453, and a plan setting function 455 by performing the above control program.

In the switching setting function 451, the processing circuitry 45 sets a switching pattern of the connections between the plurality of detector elements 51 and the plurality of DAS elements 53 by the switching control circuitry 57 in a manner so that the DAS elements 53 which are connection destinations for the respective detector elements 51 are dispersed over multiple views. The processing circuitry 45 sets a switching pattern in accordance with instructions from a user via the input circuitry 41, or sets the pattern automatically. The switching setting function 451 may be realized by the gantry control circuitry 21 or the switching control circuitry 57 provided in the gantry 10.

In the failed element specifying function 453, the processing circuitry 45 specifies a failed element from the plurality of DAS elements 53 based on pixel values of the respective pixels constituting the sinogram. An identifier of the failed element is transmitted to the gantry 10 via the I/F circuitry 37, etc. The switching control circuitry 57 switches the connections between the plurality of detector elements 51 and the plurality of DAS elements 53, avoiding the failed element.

In the plan setting function 455, the process circuitry 45 sets a scan plan automatically or in accordance with instructions from a user via the input circuitry 41. A scan plan is defined by a combination of the plurality of scan parameters constituting a scan condition. As scan parameters, for example, X-ray condition parameters and scan target regions may be used. The X-ray condition parameters include parameters defining an X-ray dosage, such as a tube current, a tube voltage, an irradiation time, etc. The data of the scan plan is transmitted to the gantry 10 via the I/F circuitry 37, etc. The switching control circuitry 57 switches between a switching mode and a non-switching mode in accordance with a dosage or a scan target region. During the switching mode, the switching control circuitry 57 switches the connections between the plurality of detector elements 51 and the plurality of DAS elements 53 at every view. During the non-switching mode, the connections between the plurality of detector elements 51 and the plurality of DAS elements 53 are stationary.

Next, the switching of the connections between the plurality of detector elements 51 and the plurality of DAS elements 53 will be explained in detail in Examples 1 to 3.

First, Example 1 is explained. In Example 1, there are the same number of the plurality of detector elements and the plurality of DAS elements.

Figure 4:
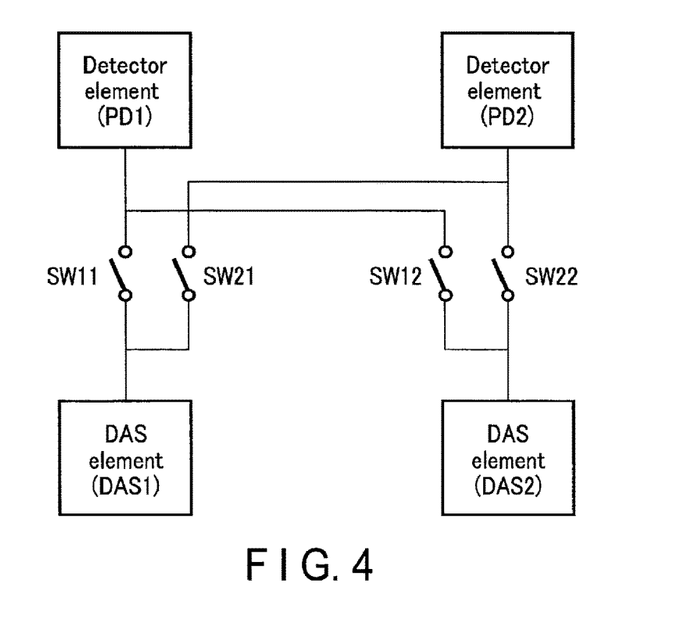
FIG. 4 is a schematic view of connections between the detector elements and the DAS elements according to Example 1.

FIG. 4 is a schematic view of the connections between the detector elements and the DAS elements according to Example 1. It should be noted that there are two detector elements 51 and two DAS elements 53 provided in the example shown in FIG. 4. Herein, a first detector element 51 is referred to as PD1, a first DAS element 53 as DAS1, a second detector element 51 as PD2, and a second DAS element 53 as DAS2. PD1 is connected to DAS1 via the switching element SW11, and to DAS2 via the switching element SW12. PD2 is connected to DAS1 via the switching element SW21, and to DAS2 via the switching element SW22. Thus, PD1 and PD2, and DAS2 1 and DAS2 are connected on a two-to-two basis.

Figure 5:
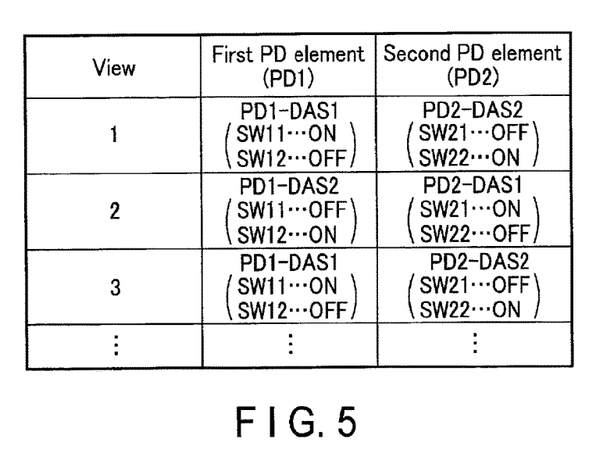
FIG. 5 shows switching patterns of the connections of the switching elements shown in FIG. 4.

FIG. 5 shows switching patterns of the connections of the switching elements shown in FIG. 4. As shown in FIG. 5, the connections between PD1 and PD2, and DAS1 and DAS2 are set in a manner so that the destination connections for PD1 and PD2 alternately switch between DAS1 and DAS2 at every view. Specifically, in view 1, PD1 is connected to DAS1 and PD2 is connected to DAS2. In other words, in view 1, SW11 closes and SW12 opens, and SW21 opens and SW22 closes. In view 2, PD1 is connected to DAS2, and PD2 is connected to DAS1. In other words, in view 2, SW11 opens and SW12 closes, and SW21 closes and SW22 opens. In view 3, PD1 is connected to DAS1, and PD2 is connected to DAS2. In other words, in view 1, SW11 closes and SW12 opens, and SW21 opens and SW22 closes.

The switching patterns of the connections between the plurality of detector elements 51 and the plurality of DAS elements 53, in other words, ON/OFF of the plurality of switching elements, are set by the processing circuitry 45 in accordance with instructions from a user via the input circuitry 41. The switching patterns are, for example, set before a scan, such as calibration. The switching patterns are stored in the main memory circuitry 43.

In the scan, the switching control circuitry 57 switches ON/OFF of the plurality of switching elements SW in accordance with the switching patterns stored in the main memory circuitry 43. The switching of views is triggered upon a supply of a view trigger signal from the view trigger generator 23. For example, in the case of switching patterns shown in FIG. 5, in view 1, the switching control circuitry 57 closes SW11 and opens SW12 to connect PD1 to DAS1, and opens SW21 and closes SW22 to connect PD2 to DAS2. Triggered by a supply of a view trigger signal from the view trigger generator 23, the switching control circuitry 57 switches the view from view 1 to view 2, then opens SW11 and closes SW12 to connect PD1 to DAS2, and closes SW21 and opens SW22 to connect PD2 to DAS1. Thus, the switching control circuitry 57 switches the plurality of switching elements SW between ON and OFF in accordance with the switching patterns.

As described above, the connections between PD1 and PD2, and DAS1 and DAS2, in other words, ON and OFF of the switching elements SW11, SW12, SW21, and SW22 are set in a manner so that the destination connections for PD1 and PD2 alternately switch between DAS1 and DAS2 at every view. By switching the output destination for each detector element 51 to the plurality of DAS elements 53 in order, the variations in properties among the detector elements 51 and the DAS elements 53 can be reduced. Thus, it is possible to reduce image artifacts due to variations in properties of the detector elements 51 and the DAS elements 53.

In Example 1 described above, there are two detector elements 51 and two DAS elements 53; it should be noted that the number of the detector elements 51 and that of the DAS elements 53 is not limited to 2 in Example 1, as long as the number is the same and is 2 or greater. For example, the detector elements 51 and the DAS elements 53 are connected via the switching circuitry 55 on a multiple-to-multiple basis, in a unit of the detector module 15M. If the detector module 15M has 24 detector elements 51 and 24 DAS elements 53, the detector elements 51 and the DAS elements 53 are connected 24-to-24 via the switching circuitry 55. In this case, by the switching control circuitry 57, each of the detector elements 51 is respectively connected in order to 24 DAS elements at every view in a manner so that the DAS elements 53, which are connection destinations, are dispersed over multiple views. Thus, by connecting each detector element 51 to a large number of DAS elements 53 included in the detector module 15M, image artifacts can be further smoothed in comparison to a case where the detector elements are connected to less DAS elements 53.

Next, Example 2 is explained. In Example 2, the number of the detector elements 51 and the number of the DAS elements 53 are not the same, and the latter is greater than the former to have redundancy in the DAS elements 53 in case of failure of a DAS element 53. There should be one or more backup DAS elements in each detector module 15M.

Figure 6:
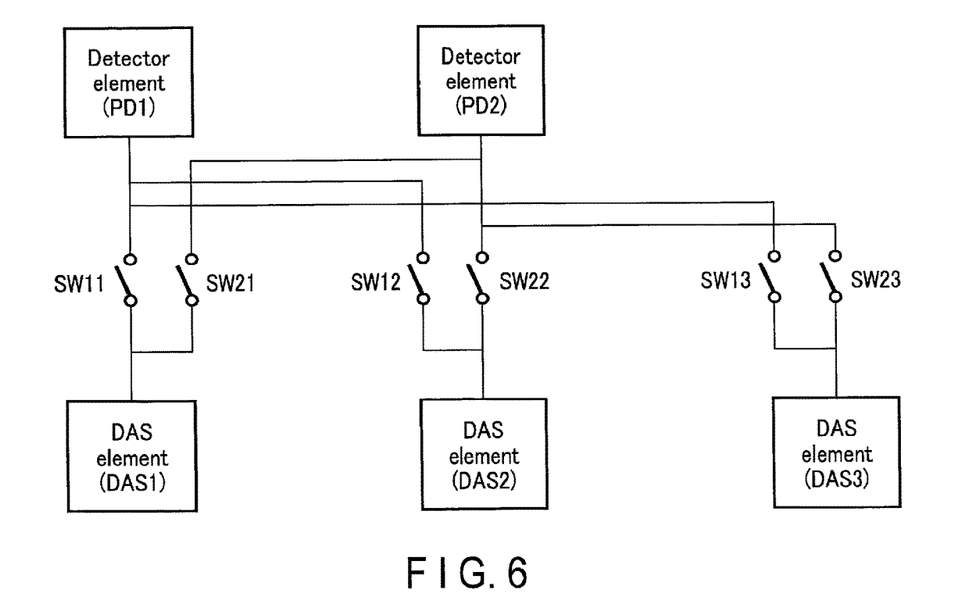
FIG. 6 is a schematic drawing of the connections between the detector elements and the DAS elements according to Example 2.

FIG. 6 is a schematic view of the connections between the detector elements and the DAS elements according to Example 2. It should be noted that there are two detector elements 51, and three DAS elements 53 are provided in the example shown in FIG. 6. Herein, a first detector element is referred to as PD1, a first DAS element as DAS1, a second detector element as PD2, a second DAS element DAS2, and a third DAS element as DAS3. PD1 is connected to DAS1 via the switching element SW11, to DAS2 via the switching element SW12, and to DAS3 via the switching element SW13. PD2 is connected to DAS1 via the switching element SW21, to DAS2 via the switching element SW22, and to DAS3 via the switching element SW23. Thus, PD1 and PD2, and DAS1, DAS2, and DAS3 are connected on a two-to-three basis. The third DAS element (DAS3) is used as a backup.

Figure 7:
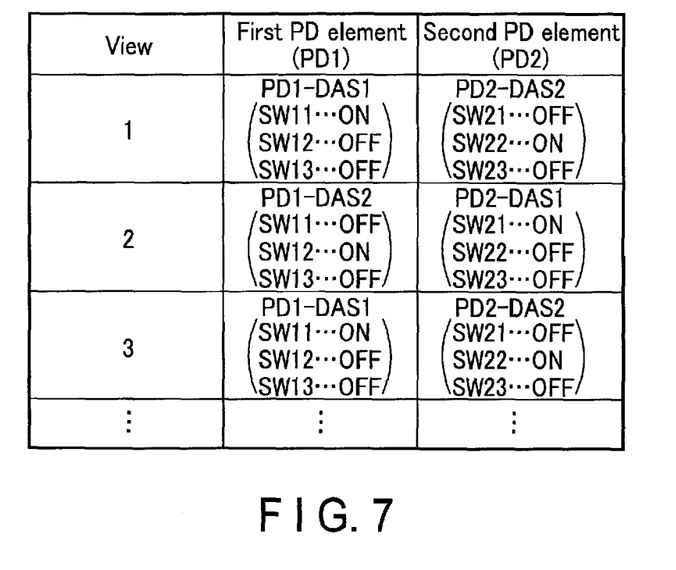
FIG. 7 shows switching patterns of the connections of the switching elements shown in FIG. 6.

FIG. 7 shows switching patterns of the connections of the switching elements shown in FIG. 6. As shown in FIG. 7, in view 1, PD1 is connected to DAS1 and PD2 is connected to DAS2. In other words, in view 1, SW11 closes, SW12 opens, SW13 opens, and SW21 opens, SW22 closes, and SW23 opens. In view 2, PD1 is connected to DAS2, and PD2 is connected to DAS1. In other words, in view 2, SW11 opens, SW12 closes and SW13 closes, and SW21 closes, SW22 opens and SW23 opens. In view 3, PD1 is connected to DAS1, and PD2 is connected to DAS2. In other words, in view 1, SW11 closes, SW12 opens, SW13 opens, and SW21 opens, SW22 closes, and SW23 opens.

Similarly to Example 1, the switching patterns of the connections between the plurality of detector elements 51 and the plurality of DAS elements 53, in other words, ON and OFF of the plurality of switching elements are set by the switching setting function 451 in accordance with instructions from a user via the input circuitry 41. The switching patterns are set before a scan, such as calibration, for example. The switching patterns are stored in the main memory circuitry 43.

Thus, the plurality of detector elements 51 are connected to the plurality of DAS elements 53 except for the backup DAS element. Specifically, the connections between PD1 and PD2, and DAS1 and DAS2, in other words, ON and OFF of the switching elements SW11, SW12, SW21, and SW22 are set in a manner so that the destination connections for PD1 and PD2 alternately switch between DAS1 and DAS2 at every view. Thus, by switching the output destination for each detector element 51 to the plurality of DAS elements 53 in order, the variations in properties among the detector elements 51 and the DAS elements 53 can be reduced. Thus, it is possible to reduce image artifacts due to variations in properties of the detector elements 51 and the DAS elements 53.

Herein, suppose that the DAS2 fails. In this case, the processing circuitry 45 resets the connection patterns to replace the failed DAS2 with deteriorated performance with the backup DAS3. Typically, the failure of a DAS element is found by a user at the time of calibration. When a failure is found, the user designates the failed DAS element via the input circuitry 41. The processing circuitry 45 sets the switching patterns of the connections between the plurality of detector elements 51 and the plurality of DAS elements 53 in a manner so that the respective detector elements 51 are connected to the respective DAS elements, except for the designated DAS element. In other words, the switching patterns of the connections between the plurality of detector elements 51 and the plurality of DAS elements 53 are set so that the designated DAS element is not connected to any of the plurality of detector elements 51. The set switching patterns after the failure are stored in the main memory circuitry 43.

Herein, the method of automatically specifying a failed DAS element is described. As described above, a failed DAS element is specified at the time of calibration. At the time of calibration, scanogram is performed under the control of the gantry control circuitry 21. In the scanogram, X-ray irradiation from the X-ray tube 12 and X-ray detect ion by the X-ray detector 15 are performed, sliding the top 171 in the Z axis direction while the rotating the still frame 11. The raw data acquired by the X-ray detector 15 during the scanogram is transmitted to the console 30. The reconstruction circuitry 33 is converted into a sinogram based on the transmitted raw data.

At the time of calibration, the processing circuitry 45 performs the failed element specifying function 453. By performing the failed element specifying function 453, the processing circuitry 45 specifies a failed DAS element from the plurality of DAS elements 53 based on pixel values of the respective pixels constituting the sinogram. The pixel value derived from the failed DAS element causes a significant difference, compared to pixel values derived from the DAS elements around the failed DAS element. The processing circuitry 45 specifies a pixel having the pixel value causing the significant difference among the plurality of pixels constituting the sinogram. It is assumed that the DAS element corresponding to the specified pixel is the failed DAS element. For example, the failed DAS element outputs raw data of a micro value or zero value over multiple views. In this case, the processing circuitry 45 performs a differentiation on the sinogram with respect to each pixel along the row direction or the channel direction, and compares the absolute value of the differentiated value with a predetermined threshold. When the differentiated absolute value is smaller than the threshold, the processing circuitry 45 determines that the DAS element 53 corresponding to the particular pixel has not failed. On the other hand, when the differentiated absolute value is greater than the threshold, the processing circuitry 45 determines that the DAS element 53 corresponding to the particular pixel has failed. An identifier of the failed element is transmitted to the gantry control circuitry 21.

During a scan, the switching control circuitry 57 switches connections between the plurality of detector elements 53 except for the failed element and the plurality of DAS elements 51.

Figure 8:
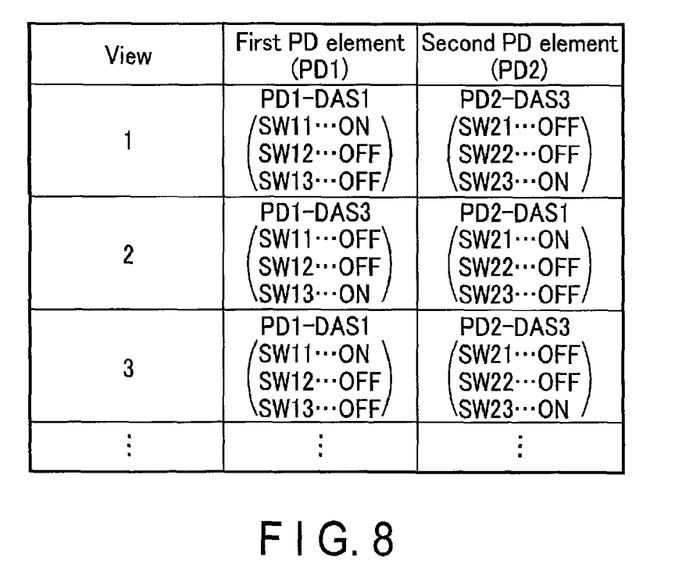
FIG. 8 shows the other switching patterns of the switching elements shown in FIG. 7 in a case of a failure in the second DAS elements (DAS2) shown in FIG. 6.

FIG. 8 shows the other switching patterns of the switching elements shown in FIG. 5 in a case of a failure in the second DAS elements (DAS2). As shown in FIG. 8, in view 1, PD1 is connected to DAS1, and PD2 is connected to DAS3. In other words, in view 1, SW11 closes, SW12 opens and SW13 opens, and SW21 opens, SW22 opens and SW23 closes. In view 2, PD1 is connected to DAS3, and PD2 is connected to DAS1. In other words, in view 2, SW11 opens, SW12 opens and SW13 closes, and SW21 closes, SW22 opens and SW23 opens. In view 3, PD1 is connected to DAS1, and PD2 is connected to DAS3. In other words, in view 1, SW11 closes, SW12 opens, SW13 opens, and SW21 opens, SW22 opens and SW23 closes. The set switching patterns after the failure are stored in the main memory circuitry 43.

In the scan after the failure, the switching control circuitry 57 switches the plurality of switching elements SW between ON and OFF in accordance with the switching patterns stored in the main memory circuitry 43. The switching patterns used for the scan can be selected by a user via the input circuitry 41. For example, in the case of switching patterns shown in FIG. 8, in view 1, the switching control circuitry 57 first closes SW11, opens SW12 and opens SW13 to connect PD1 to DAS1, and then opens SW21, closes SW22 and closes 23 to connect PD2 to DAS3. Triggered by a supply of a view trigger signal from the view trigger generator 23, the switching control circuitry 57 switches the view from view 1 to view 2, then opens SW11, opens SW12, and closes SW13 to connect PD1 to DAS3, and closes SW21 and opens SW22, and opens SW23 to connect PD2 to DAS1.

As described above, the processing circuitry 45 according to Example 2 sets switching patterns of the connections between the plurality of detector elements 51 and the plurality of DAS elements 53, avoiding a DAS element 53 with a deteriorated performance, such as a failed DAS element 53. Having more DAS elements 53 than the detector elements 51 in the DAS 153, the switching control circuitry 57 can control the switching circuitry 55 even when a DAS element 53 fails to connect each detector element 51 to the DAS element 53, avoiding the failed DAS element. Thus, it becomes possible to reduce image artifacts due to the failed DAS element 53. Compared to a case where there are the same number of the DAS elements 53 and the detector elements 51, it is possible to reduce the frequency of changing the detector module 15M or the X-ray detector 15, thereby reducing a failure rate of the detector module 15M or the X-ray detector 15 from a user's viewpoint.

In Example 2 described above, there are two detector elements 51 and three DAS elements 53; it should be noted that the number the detector elements 51 and that of the DAS elements 53 are not limited to 2 and 3 in Example 2, as long as the number is 2 or greater, and there are more DAS elements 53 than the detector elements 51. For example, the detector elements 51 and the DAS elements 53 are connected via the switching circuitry 55 on a multiple-to-multiple basis, in a unit of the detector module 15M. If the detector module 15M has 24 detector elements 51 and 25 DAS elements 53, the detector elements 51 and the DAS elements 53 are connected 24-to-25 via the switching circuitry 55. In this case, by the switching control circuitry 57, each of the detector elements 51 is connected in order to 24 DAS elements, except for the backup DAS element, at every view in a manner so that the DAS elements 53, which are connection destinations, are dispersed over multiple views. Thus, by connecting each detector element 51 to a large number of DAS elements 53 included in the detector module 15M, image artifacts can be further smoothed in comparison to a case where the detector elements are connected in order to less DAS elements 53.

Next, Example 3 is explained. Example 3 is a variation of Example 2. In Example 2, the switching pattern is set in a manner so that the backup DAS element (DAS3 in FIG. 6) is not connected to a detector element before a DAS element fails. In contrast, in Example 3, a switching pattern is set in a manner so that the backup DAS element is connected to a detector element.

Figure 9:
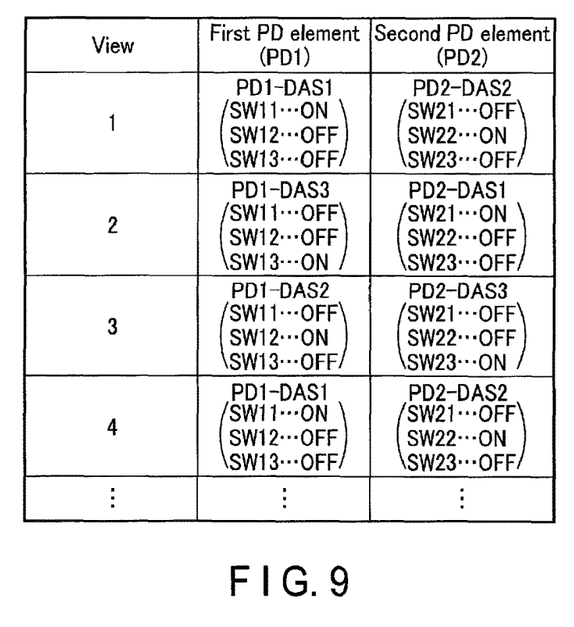
FIG. 9 shows switching patterns of the connections of the switching elements according to Example 3.

FIG. 9 shows switching patterns of the connections of the switching elements SW according to Example 3. As shown in FIG. 9, in view 1, PD1 is connected to DAS1 and PD2 is connected to DAS2. In other words, in view 1, SW11 closes, SW12 opens, SW13 opens, and SW21 opens, SW22 closes, and SW23 opens. In view 2, PD1 is connected to DAS3, and PD2 is connected to DAS1. In other words, in view 2, SW11 opens, SW12 opens and SW13 closes, and SW21 closes, SW22 opens and SW23 opens. In view 3, PD1 is connected to DAS2, and PD2 is connected to DAS3. In other words, in view 1, SW11 opens, SW12 closes and SW13 opens, and SW21 opens, SW22 opens and SW23 closes. In view 4, PD1 is connected to DAS1, and PD2 is connected to DAS2. In other words, in view 4, SW11 closes, SW12 opens, SW13 opens, and SW21 opens, SW22 closes, and SW23 opens.

As described above, the respective detector elements 51 are connected to the plurality of DAS elements 53 including the backup DAS element 53 over multiple views in a dispersed manner. Thus, it is possible to further reduce variations in properties of the detector elements 51 and the DAS elements 53 in comparison with Example 2.

When DAS2 fails, the processing circuitry 45 can reset the switching patterns so that failed DAS2 can be replaced with the backup DAS3, as disclosed in Example 2. In other words, the processing circuitry 45 sets the switching patterns at every view of the connections between the plurality of detector elements 51 and the plurality of DAS elements 53 in a manner so that the designated DAS element is not connected to any of the plurality of detector elements, like the switching patterns shown in FIG. 8. The explanation of the operation of the switching control circuitry 57 in accordance with the switching patterns after the failure, which is the same as that disclosed in Example 2, is omitted.

This concludes the explanation of Examples 1, 2, and 3.

It should be noted that all of the detector elements 51 and the DAS elements 53 of the X-ray detector 15 are connected on a multiple-to-multiple basis. However, the present embodiment is not limited thereto. Because of the characteristics of the X-ray computed tomography apparatus, image artifacts stand out in the center area of an image; accordingly, only the detector elements 51 and the DAS elements 53 in the image center area may be connected on a multiple-to-multiple basis, and the detector elements 51 and the DAS elements 53 outside in the image center area may be connected to a one-to-one basis.

Figure 10:
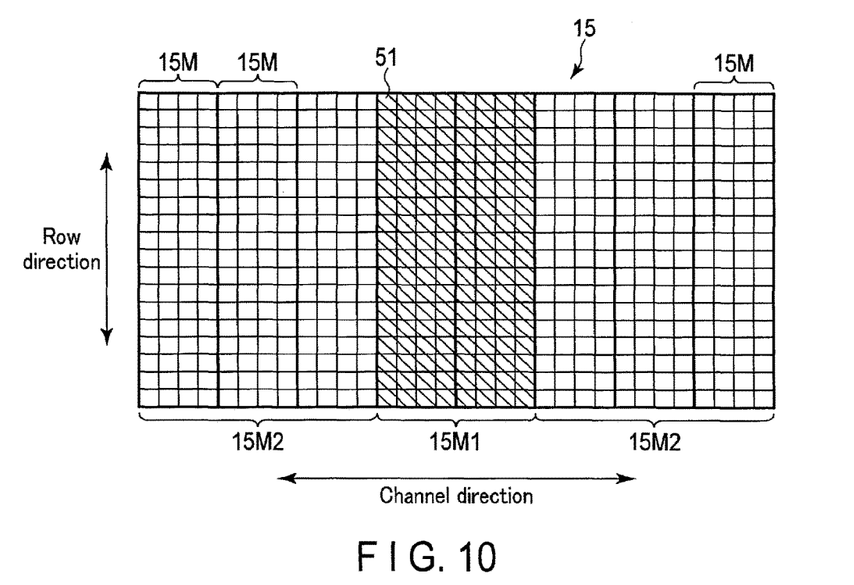
FIG. 10 is a plane view of distribution of the multiple-to-multiple connection relationship and the one-to-one connection relationship in the X-ray detector according to the present embodiment.

FIG. 10 is a plane view of the distribution of the multiple-to-multiple connection relationship and the one-to-one connection relationship in the X-ray detector 15. As shown in FIG. 10, the image center area where the detector elements 51 and the DAS elements 53 are connected on a multiple-to-multiple basis corresponds to, for example, the detector module 15M1 which is located at the center area with respect to the channel direction of the X-ray detector 15. In this case, only the detector elements 51 and the DAS elements 53 included in the detector module 15M1 are connected on a multiple-to-multiple basis via the switching circuitry 55. The detector elements 51 and the DAS elements 53 included in the other detector module 15M2 are directly connected on a one-to-one basis, without the switching circuitry 55. It should be noted that, in the above, the image center area in FIG. 10 was defined as the center area with respect to the channel direction; however, the image center area may be a center area with respect to the row direction. Thus, by connecting the elements on a multiple-to-multiple basis only in the image center area, costs involved in switching the switching elements, for example, can be reduced.

The connections between the plurality of detector elements 51 and the plurality of DAS elements 53 in the above embodiment switch in single view units; however, the connections may switch in multiple view units (2 or greater). Thus, it is possible to reduce noise due to the switching of the switching elements included in the switching circuitry 55 between ON and OFF.

It should be noted that the switching control circuitry 57 may switch between a switching mode and a non-switching mode in accordance with a dosage or a scan target region. During a switching mode, the connections between the plurality of detector elements 51 and the plurality of DAS elements 53 switch at every predetermined view. During the non-switching mode, the connections between the plurality of detector elements 51 and the plurality of DAS elements 53 are stationary.

The dosage and scan target region are set by the processing circuitry 45 by executing the plan setting function 455. The data of the set dosage or scan target region is transmitted to the gantry 10 via the I/F circuitry 37, etc.

The less the dosage is, the more artifacts due to a low dosage will occur in a CT image. Thus, if a user wants to prevent any more artifacts when he performs a scan under a low dosage, the switching control circuitry 57 is set in a switching mode only when a dosage is relatively low, and is set in a non-switching mode when a dosage is not relatively low. Specifically, the switching control circuitry 57 compares the dosage set by the plan setting function 455 with a predetermined threshold. The dosage of 100 mA is a low dosage, and the dosage of 500 mA is considered to be a high dosage; accordingly, a threshold should be set at 300 mA. It should be noted that the threshold can be set at an arbitrary value via the input circuitry 41, etc. When the dosage is higher than the threshold, the switching control circuitry 57 is set in a non-switching mode. When the dosage is lower than the threshold, the switching control circuitry 57 is set in a non-switching mode.

In the above example, the switching control circuitry 57 is set in a non-switching mode when the dosage is higher than the threshold, and is set in a switching mode when the dosage is lower than the threshold. However, the present embodiment is not limited thereto.

An artifact due to a living body may occur in a CT image, depending on a scan target region. For example, when the pelvic region, which includes large bones, is the scan target region, many artifacts will occur due to X-ray scattering caused by the bones in the pelvic region. The switching control circuitry 57 is set in a switching mode only when a scan target region is set in which artifacts easily occur, and the switching control circuitry 57 is set in a non-switching mode when a scan target region is set in which artifacts do not easily occur. Specifically, the switching control circuitry 57 stores a lookup table (LUT) in which a code for performing a switching mode and a code for performing a non-switching mode are associated among the codes for a plurality of scan target regions. For example, in the LUT, a code for the pelvic region in which artifacts easily occur is associated with a code for performing a switching mode. Upon setting the scan target region by the plan setting function 455, the switching control circuitry 57 determines a mode in accordance with the set scan target region, using the LUT. For example, when the pelvic region is the scan target region, the code for the pelvic region is associated with a code for performing a switching mode in the LUT; thus, the switching control circuitry 57 is set in a switching mode. When a code for the scan target region is associated with a code for performing a switching mode, the switching control circuitry 57 is set to a switching mode. When a code for the scan target region is associated with a code for performing a switching mode, the switching control circuitry 57 is set to a non-switching mode.

When a switching mode is set as a result of the above process, in a scan, the switching control circuitry 57 switches the connections between the plurality of detector elements 51 and the plurality of DAS elements 53 at every predetermined view. When a non-switching mode is set, the switching control circuitry 57 makes the connections between the plurality of detector elements 51 and the plurality of DAS elements 53 stationary. As a consequence, the switching control circuitry 57 can switch the connections between the plurality of detector elements 51 and the plurality of DAS elements 53, only when a dosage or a scan target region in which artifacts easily occur is set.

In the above processing, the switching control circuitry 57 is set in a switching mode when a dosage or a scan target region in which artifacts easily occur is set. However, it should be noted that the switching control circuitry 57 may be arbitrarily set in a switching mode and a non-switching mode, regardless of dosage or a scan target region, in accordance with the user's instructions via the input circuitry 41, etc. For example, even when a scan is performed under a high dosage, if a user wants to generate a high-quality CT image, the switching control circuitry 57 may be set in a switching mode.

In the above explanation, the X-ray computed tomography apparatus is a so-called third-generation apparatus. In other words, the X-ray computed tomography apparatus is a rotate/rotate-type apparatus in which the X-ray tube 13 and the X-ray detector 15 integrally rotate around the subject S. However, the X-ray computed tomography apparatus according to the present embodiment is not limited thereto. For example, the X-ray computed tomography apparatus may be a stationary/rotate-type apparatus in which the large number of detector elements and DAS elements aligned in a ring-shape are stationary, and only the X-ray tube 13 rotates around the subject S.

As described above, the X-ray computed tomography apparatus according to the present embodiment includes the X-ray tube 13, the plurality of detector elements 51, and the plurality of DAS elements 53, and the switching circuitry 55, and the switching control circuitry 57. The X-ray tube 13 generates X-rays. The plurality of detector elements 51 detect X-rays. The plurality of DAS elements 53 perform signal processing on output signals from the plurality of detector elements 51. The switching circuitry 55 is provided between the plurality of detector elements 51 and the plurality of DAS elements 53. The switching control circuitry 57 controls the switching circuitry 55 to switch the connections between the plurality of detector elements 51 and the plurality of DAS elements 53 at every view.

According to the above configuration, the plurality of detector elements 51 and the plurality of DAS elements 53 can be connected on a multiple-to-multiple basis via the switching circuitry 55. Thus, it is possible to reduce image artifacts due to the variations in properties among the detector elements 51 and the DAS elements 53 by dispersing the plurality of DAS elements which are the connection destinations for the respective detector elements 51, over multiple views. Therefore, it is possible to reduce the frequency of replacing the X-ray detector 15 or the detector module 15M. When the X-ray detector 15 or the detector module 15M is replaced, it is necessary to perform calibration; on the other hand, it is possible to reduce the frequency of calibration by reducing the frequency of replacement.

Therefore, according to the present embodiment, a reduction of image artifacts due to the variations in properties among the detector elements and DAS elements can be realized.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus, comprising:
    an X-ray tube configured to generate X-rays;
    a rotating frame to which the X-ray tube is attached;
    a plurality of detector elements configured to detect X-rays;
    a plurality of DAS elements configured to perform signal processing on output signals from the plurality of detector elements;
    switching circuitry provided between the plurality of detector elements and the plurality of DAS elements; and
    switching control circuitry configured to control the switching circuitry in a manner to switch connections between the plurality of detector elements and the plurality of DAS elements for every rotation of the rotating frame at a predetermined angle,
    wherein the switching control circuitry is further configured to control the switching circuitry to switch, for each detector element, a DAS element, of the plurality of DAS elements, that is a connection destination for the detector element.

2. The X-ray computed tomography apparatus according to claim 1, further comprising:
    a drive device configured to generate power to rotate the rotating frame; and trigger signal generating circuitry configured to generate a trigger signal for every rotation of the rotating frame at the predetermined angle corresponding to a period of view, wherein the switching control circuitry is configured to switch the connections between the plurality of detector elements and the DAS elements using generation of a trigger signal corresponding to the predetermined view as a reference.

3. The X-ray computed tomography apparatus according to claim 1, wherein the plurality of detector elements and the plurality of DAS elements are connected on a multiple-to-multiple basis.

4. The X-ray computed tomography apparatus according to claim 1, wherein first detector elements included in a predetermined range of the plurality of detector elements are connected to first DAS elements included in a predetermined range of the plurality of DAS elements on a multiple-to-multiple basis; and second detector elements included outside of the predetermined range of the plurality of detector elements are connected to second DAS elements included outside of the predetermined range of the plurality of DAS elements on a one-to-one basis.

5. The X-ray computed tomography apparatus according to claim 4, wherein the predetermined range is approximately set at a central part with respect to a channel direction.

6. The X-ray computed tomography apparatus according to claim 1, wherein a number of the plurality of detector elements is a same as a number of the plurality of DAS elements.

7. The X-ray computed tomography apparatus according to claim 1, wherein a number of the plurality of DAS elements is greater than a number of the plurality of detector elements.

8. The X-ray computed tomography apparatus according to claim 1, further comprising processing circuitry configured to set the connections between the plurality of detector elements and the plurality of DAS elements.

9. The X-ray computed tomography apparatus according to claim 8, wherein the processing circuitry sets the connections between the plurality of detector elements and the plurality of DAS elements in a manner so that the respective detector elements are connected to the respective DAS elements, except for a DAS element which has a deteriorated performance.

10. The X-ray computed tomography apparatus according to claim 1, wherein each of the plurality of detector elements includes a scintillator absorbing X-rays emitting fluorescence and an optical detector converting the fluorescence into an electric signal, and each of the plurality of DAS elements includes an integrator integrating the electric signal and an A/D converter converting the integrated electric signal into a digital signal.

11. The X-ray computed tomography apparatus according to claim 1, wherein the switching control circuitry is further configured to switch between a switching mode and a non-switching mode in accordance with a dosage or a scan target region, during a switching mode, the connections between the plurality of detector elements and the plurality of DAS elements switch at every predetermined view, and during a non-switching mode, the connections between the plurality of detector elements and the plurality of DAS elements are stationary.

12. The X-ray computed tomography apparatus according to claim 1, wherein the switching control circuitry is set in the switching mode when a dosage is lower than a predetermined threshold, and is set in the non-switching mode when the a dosage is higher than the threshold.

13. The X-ray computed tomography apparatus according to claim 1, wherein the switching control circuitry is set in the switching mode when a scan target region is a part in which artifacts easily occur, and is set in the non-switching mode when a scan target region is a part in which artifacts do not easily occur.

14. The X-ray computed tomography apparatus according to claim 1, further comprising:

reconstruction circuitry configured to generate a sinogram based on an output from the plurality of DAS elements; and processing circuitry configured to specify a failed element from the plurality of DAS elements based on pixel values of respective pixels constituting the sinogram, wherein the switching control circuitry is configured to switch connections between the plurality of detector elements except for the failed element and the plurality of DAS elements.

15. An X-ray detector, comprising:

a plurality of detector elements configured to detect X-rays;

a plurality of DAS elements configured to perform signal processing on output signals from the plurality of detector elements;

a plurality of switches provided between the plurality of detector elements and the plurality of DAS elements; and switching control circuitry configured to control the plurality of switches in a manner so that connections between the plurality of detector elements and the plurality of DAS elements switch at every view, wherein the switching control circuitry is further configured to control the switching circuitry to switch, for each detector element, a DAS element, of the plurality of DAS elements, that is a connection destination for the detector element.

* * * * *